(12) United States Patent
Baeuerle et al.

(10) Patent No.: US 7,871,575 B2
(45) Date of Patent: Jan. 18, 2011

(54) HANDLING UNIT FOR MICROFLUIDIC DEVICES

(75) Inventors: Martin Baeuerle, Buehlertal (DE); Hans-Georg Weissgerber, Straubenhardt (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1161 days.

(21) Appl. No.: 11/385,095

(22) Filed: Mar. 21, 2006

(65) Prior Publication Data

US 2007/0025887 A1 Feb. 1, 2007

(30) Foreign Application Priority Data

Jul. 15, 2005 (EP) .................................. 05106506

(51) Int. Cl.
*B01L 9/00* (2006.01)

(52) U.S. Cl. ...................... 422/104; 422/68.1; 422/99; 422/100; 204/601; 204/602

(58) Field of Classification Search ........... 422/99–100, 422/68.1, 104; 204/601–602
See application file for complete search history.

(56) References Cited

U.S. PATENT DOCUMENTS

| 5,266,275 A | * | 11/1993 | Faddis | .......................... 422/116 |
| 6,323,035 B1 | | 11/2001 | Kedar et al. | .................... 436/43 |
| 6,495,104 B1 | * | 12/2002 | Unno et al. | ................. 422/68.1 |
| 2005/0037485 A1 | | 2/2005 | Rodgers et al. | |

FOREIGN PATENT DOCUMENTS

| WO | WO 2004/055521 | 7/2004 |
| WO | WO 2005/102509 | 11/2005 |

* cited by examiner

*Primary Examiner*—Jyoti Nagpaul (57) ABSTRACT

A handling unit that comprises a first clamping element and a second clamping element, and an actuation mechanism adapted for driving at least one of the clamping elements. When the at least one of the clamping elements is driven to a first position, a microfluidic device may be placed between the clamping elements or taken out of the clamping elements, and when the at least one of the clamping elements is driven to a second position, the microfluidic device is gripped and fastened by the clamping elements.

14 Claims, 4 Drawing Sheets

HANDLING UNIT FOR MICROFLUIDIC DEVICES

BACKGROUND ART

1. Field of the Invention

The present invention relates to a handling unit adapted for handling a microfluidic device, and to a method for detachably fastening a microfluidic device in a handling unit.

2. Discussion of the Background Art

U.S. Pat. No. 5,872,010, "Microscale Fluid Handling System" to B. L. Karger discloses a microchip fluid handling system including one or more exit ports integral with the end of one or more of the channels for consecutive or simultaneous off-chip analysis or collection of the sample.

International Patent Application WO 2004/050620 relates to a microfluidic connection, and International Patent Application WO 2004/050893 relates to a microfluidic chip adapted for executing at least two processes in parallel. European Patent Application EP 05100768.0 discloses a frame for microfluidic chips, and European Patent Application EP 04102250.0 is related to a microfluidic valve with a first and a second revolving valve element.

SUMMARY OF THE INVENTION

It is an object of the invention to improve the handling of microfluidic devices.

A handling unit according to embodiments of the present invention is adapted for handling a microfluidic device and comprises a first clamping element, a second clamping element, and an actuation mechanism adapted for driving at least one of the clamping elements. When the at least one of the clamping elements is driven to a first position, a microfluidic device may be placed between the clamping elements or taken out of the clamping elements. When the at least one of the clamping elements is driven to a second position, the microfluidic device is gripped and fastened by the clamping elements.

When the clamping elements are located at their respective first positions, they are spaced apart from one another. Hence, it is possible to place a microfluidic device between the two clamping elements, or to remove a microfluidic device from the handling unit. Then, one or both of the clamping elements may be driven to respective second positions, whereby the microfluidic device is gripped and tightly fixed at a predefined position. After the microfluidic device has been gripped, operation of the microfluidic device may be started. For example, a series of measurements may be performed. After operation of the microfluidic device has been finished, one or both of the clamping elements may be driven back to their respective first positions, thereby releasing the microfluidic device. Now, the microfluidic device may be taken out of the handling unit.

By driving the clamping elements to their second positions, the microfluidic device is tightly fastened. Thus, it is possible to keep the microfluidic device at a precisely defined position relative to a laboratory apparatus, and precision of the measurements is improved. Another advantage is that the handling unit allows performing the tasks of fastening and unfastening the microfluidic device in an automated manner. For example, after the microfluidic device has been inserted between the two clamping elements, the actuation mechanism might automatically drive the clamping elements from their first positions to their second positions, thus fastening the microfluidic device. After operation has been finished, the actuation mechanism might automatically drive the clamping elements back to their first positions, thereby releasing the microfluidic device.

Thus, the actuation mechanism is adapted for tightening the microfluidic device by driving the at least one of the clamping elements towards its second position, and for untightening the microfluidic device by driving the at least one of the clamping elements towards its second position. By forwarding respective control commands to the actuation mechanism, the tasks of fastening and unfastening the microfluidic device may be performed automatically. Thus, the handling unit according to embodiments of the present invention contributes to an automated handling of microfluidic devices, which can be a prerequisite for automatically carrying out a complex sequence of measurement methods.

In a preferred embodiment, when the clamping elements are driven to their second positions, they are tightly pressed against the microfluidic device, with the actuation mechanism being adapted for exerting a predefined contact pressure upon the microfluidic device's surface. Thus, the microfluidic device is tightly gripped and fixed at a predefined position.

In a preferred embodiment, one of the clamping elements is a stationary clamping element, whereas the other clamping element is a movable clamping element adapted for being driven by the actuation mechanism. This might simplify the mechanical setup. Alternatively, both clamping elements might be implemented as movable clamping elements. This allows for a symmetrical fastening of the microfluidic device.

According to a preferred embodiment, the microfluidic device comprises a microfluidic chip supported by a frame, the frame being adapted for protecting the microfluidic chip. For example, in case the microfluidic chip is made of a flexible polymeric material, the frame improves the microfluidic chip's mechanical stability. In case the microfluidic chip comprises an electrospray nozzle, the frame prevents damages of the electrospray nozzle.

In a further preferred embodiment, at least one of the clamping elements comprises alignment features adapted for aligning the microfluidic device with the clamping elements. For example, one of the clamping elements might comprise one or several alignment rods that extend through corresponding catch holes of the microfluidic device when driving the clamping elements towards the microfluidic device. During the process of fastening the microfluidic device, the microfluidic device is aligned relative to the clamping elements. Hence, after the microfluidic device has been gripped, it is exactly located at a predefined position.

In a preferred embodiment, the actuation mechanism is realized using threaded spindles that are driven by stepper motors, with at least one of the clamping elements comprising a screw nut engaged with a threaded spindle. The stepper motor may control the spindle's rotation with great angular precision. The threaded spindle is adapted for translating this rotary motion into a corresponding linear movement of the at least one of the clamping elements. Thus, the clamping elements can be positioned with great accuracy. Furthermore, the stepper motor might be capable of exerting a certain angular momentum upon the threaded spindle, with this angular momentum being translated into a contact pressure exerted upon the microfluidic device.

In a preferred embodiment, at least one of the clamping elements is adapted for establishing one or more hydraulic connections with the microfluidic device when the at least one of the clamping elements is pressed against the microfluidic device's surface. In a further preferred embodiment, at least one of the clamping elements comprises one or more fluid connectors adapted for establishing fluid connections with corresponding fluid ports when the microfluidic device is fastened. When the microfluidic device is gripped, the fluid connectors are tightly pressed against the inlets and/or outlets of the microfluidic device, and fluid-tight connections are set up. Via these connections, different kinds of fluids, like e.g. solvents, sample fluid, etc. may be supplied to the microfluidic device via one or several fluid supply lines. Furthermore, waste flows may be removed from the chip via the fluid connections.

Using a handling unit according to embodiments of the present invention, fluid connections to the microfluidic device can be set up and detached in a quick and convenient manner. The microfluidic device is mechanically fastened by driving the clamping elements from their first positions to their second positions, and simultaneously, the required fluid connections are established. Even if the microfluidic device's operation requires to set up a large number of fluid connections, the required fluid connections can be set up by simply gripping the microfluidic device. Connecting a microfluidic device is no longer a cumbersome task.

In a preferred embodiment, fluids are supplied to the microfluidic device at pressures of 100 bar and above. In modern microfluidic devices, dimensions of the fluid conduits get smaller and smaller, flow rates are reduced, and system pressure is steadily increasing. Currently, pressures of about 400 bar are used, whereas in future applications, it can become necessary to use pressures of about 800 bar. Even at pressures that are that high, the handling unit is capable of providing a fluid-tight coupling between the fluid connectors of a clamping element and the fluid ports of the microfluidic chip. For example, the microfluidic chip may be made of polymeric material. If the contact pressure of the clamping elements is sufficiently high, the fluid connectors will be tightly pressed against the openings of the microfluidic chip, and fluid-tight connections can be established without using any additional sealing elements. Hence, the handling unit is capable of dealing with the fluid pressures required for future microfluidic devices.

In a preferred embodiment, the actuation forces exerted by the actuation mechanism are sufficiently high for generating the required contact pressure. For example, in case of a threaded rod being driven by a stepper motor, the stepper motor's angular momentum has to be high enough for generating the required chucking power.

According to a preferred embodiment, at least one of the clamping element is deformed when being pressed onto the microfluidic chip's surface. As a result, the respective clamping element will exert an additional force upon the microfluidic device, with the additional force being due to the deformation. For example, at least one of the clamping elements might act as a spring bolt that is bent when being driven towards the microfluidic device. This extra spring force improves the chucking power of the clamping elements.

In another preferred embodiment, at least one of the clamping elements is adapted for establishing one or more electrical connections with the microfluidic device when being pressed against the microfluidic device. For example, the clamping element might comprise spring-loaded contact pins that are pressed against corresponding contact pads of the microfluidic device. Thus, required voltages and/or currents may be supplied to the microfluidic device. For example, in case an electrophoresis column is used for separating compounds of a given sample, a voltage is required for driving the charged ions through the separation column. The electrical connections with the microfluidic device's contact pads are established when the microfluidic device is gripped by the clamping units, and hence, no further user interaction is required for establishing the required connections.

In a further preferred embodiment, at least one of the clamping elements comprises one or more of: a heating element, a cooling element, a thermal element, a Peltier element. When the clamping element is driven towards the microfluidic device's surface, the respective element is tightly pressed against a corresponding part of the microfluidic device. The respective element might e.g. be responsible for cooling the microfluidic device. Alternatively or additionally, the respective element might be adapted for supplying a predefined amount of heat to the microfluidic chip. Preferably, a Peltier element is employed, which can be used both for heating and cooling the microfluidic device.

Hence, one or more of the handling unit's clamping elements may be suited for establishing at least one of hydraulic, electrical and thermal connections when being pressed against the microfluidic device. At the same time when the microfluidic device is fastened by the clamping elements, the required hydraulic, electrical and thermal connections are established instantaneously. After the microfluidic device's operation, when the clamping elements are driven back to their respective first positions, the respective hydraulic, electrical and thermal connections are detached.

In a preferred embodiment, at least one of the clamping elements comprises a rotor element that is tightly pressed against the microfluidic device when the clamping element is driven towards the microfluidic device. The rotor element's face comprises a number of groups that provide fluid connections between adjacent stator ports when the rotor element is pressed against the microfluidic device. By rotating the rotor element to various different positions, it is possible to switch between different flow paths of the microfluidic device.

In a preferred embodiment, the rotor element is part of a multiport switching valve. In a further preferred embodiment, at least one of the clamping elements comprises a rotor plate adapted for accommodating the rotor element. Further preferably, the rotor plate is mounted to the clamping element using a bold joint coupling, in order to allow for an angular adjustment of the rotor plate when the rotor plate is pressed against the microfluidic device. Thus, the grip of the clamping elements is improved.

According to a preferred embodiment, the position of the clamping elements and of a microfluidic device that may be contained therein are varied using a positioning device. Preferably, the positioning device comprises one or more linear drives. Further preferably, the positioning device is adapted for positioning both the clamping elements and a microfluidic device contained therein relative to an external laboratory apparatus. For example, the positioning device may be adapted for positioning the microfluidic device relative to the entrance slit of a mass spectroscopy unit.

In a further preferred embodiment, the positioning device's linear drives may be equipped with one or more encoders, with the encoders supplying positioning signals indicative of the linear drives' actual positions. In response to these positioning signals, a control unit may accurately position a microfluidic device relative to a laboratory apparatus.

In a preferred embodiment, the positioning device is utilized for positioning the microfluidic device relative to a mass spectroscopy unit. In this embodiment, variations of the voltage-current-characteristic recorded at the mass spectroscopy unit's target electrode may be used as a starting point for adjusting the microfluidic device's position relative to the mass spectroscopy unit.

In a preferred embodiment, the handling unit further comprises a robotic manipulator adapted for transferring microfluidic devices from a repository to the clamping elements, and, after operation has been finished, from the clamping elements back to the repository. In a preferred embodiment, the handling unit comprises a storage rack adapted for storing a multitude of microfluidic devices. The robotic manipulator may select one of the microfluidic devices stored in the storage rack. In a further preferred embodiment, the storage rack may comprise microfluidic devices of different types. For example, the storage rack might comprise microfluidic devices suited for different analytical tasks. The various microfluidic devices may comprise separation columns of different sizes filled with different kinds of packing materials. From the various microfluidic devices, the robotic manipulator may select the one that is best-suited for the respective analytical task.

According to a further preferred embodiment, the robotic manipulator is adapted for performing one or more of the following: selecting a microfluidic device from the storage rack, gripping a microfluidic device, transferring the microfluidic device from the storage rack to a location between the clamping elements, placing the microfluidic device between the clamping elements, aligning the microfluidic device with the clamping elements, removing a microfluidic device from the location between the clamping elements, and transferring the microfluidic device from the clamping elements back to the storage rack.

In a preferred embodiment, the handling unit is adapted for evaluating a feedback signal, with the feedback signal being adapted for initiating replacement of the microfluidic device. According to another preferred embodiment, the feedback signal indicates wear of the microfluidic device. When degradation of the microfluidic device is detected, the handling unit will replace the former microfluidic device by a new microfluidic device.

In a preferred embodiment, the feedback signal indicates at least one of actual flow and actual fluid pressure within the microfluidic device. The microfluidic device might e.g. comprise detection units adapted for determining these quantities. In a further preferred embodiment, the feedback signal might indicate a quality of obtained measurement results, in particular a signal-to-noise level of acquired spectra.

In a further preferred embodiment, the handling unit further comprises a control unit adapted for generating control commands for one or more of: the actuation mechanism, the positioning device, the robotic manipulator device. Using the control unit, a sequence of handling may be executed automatically. For example, a series of consecutive measurements may be performed automatically, wherein the robotic manipulator may exchange the microfluidic device between different measurements.

Embodiments of the invention can be partly or entirely embodied or supported by one or more suitable software programs, which can be stored on or otherwise provided by any kind of data carrier, and which might be executed in or by any suitable data processing unit. Software programs or routines are preferably applied for controlling the handling unit.

BRIEF DESCRIPTION OF THE DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

DETAILED DESCRIPTION OF THE PREFERRED EMBODIMENT

Figure 1:
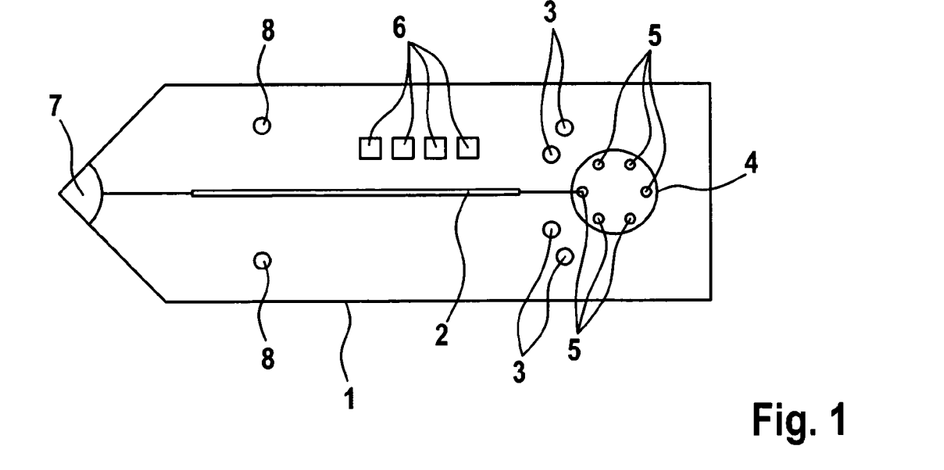
FIG. 1 shows a microfluidic chip.

FIG. 1 shows a microfluidic chip 1 comprising one or more microfluidic flow paths. The microfluidic chip 1 shown in FIG. 1 comprises a separation column 2, said separation column 2 being adapted for separating compounds of a sample of interest. For analyzing a given sample, techniques such as e.g. electrophoresis or liquid chromatography might be employed, with the separation column 2 being filled with some kind of packing material. The microfluidic chip 1 might further comprise fluid ports 3 adapted for supplying various fluids like e.g. solvents, eluents, sample etc. to the chip's flow paths, and for carrying off waste flows. Because of the ever decreasing dimensions of microfluidic flow paths, it might be necessary to supply fluids at pressures of 100 bar and above. The microfluidic chip 1 might further comprise a multi-route switching valve adapted for switching between different flow paths. The multi-route switching valve comprises a rotor element 4 that is tightly pressed onto the fluid ports 5 of the microfluidic chip, which acts as a stator. By rotating the rotor element 4 to different positions, it is possible to switch between different fluid connections of the fluid ports 5.

Required voltages and/or currents may be applied via a set of contact pads 6. For example, in case of electrophoresis being used for separating sample compounds, the voltage required for driving ionized species through the separation column 2 may be applied to the contact pads 6. In the example of FIG. 1, the microfluidic chip 1 further comprises an electrospray nozzle 7 that is fluidly connected with the separation column's outlet. The electrospray nozzle 7 is adapted for ionizing species obtained from the separation column 2, and for providing a spray of ionized species to an external mass spectroscopy unit.

The microfluidic chip 1 may be made of different layers of polymeric foil. First, these polymeric foils are microstructured using techniques such as hot embossing, laser ablation, etc. Then, the different polymeric foils are assembled, in order to form a microfluidic chip device. Preferably, for the different layers, materials such as e.g. polyimide or PEEK (Polyether Ether Ketone) are used. The microfluidic chip 1 might further comprise catch holes 8 that extend through the entire chip. These catch holes 8 are used for aligning and fixing the microfluidic chip 1.

Figure 2:
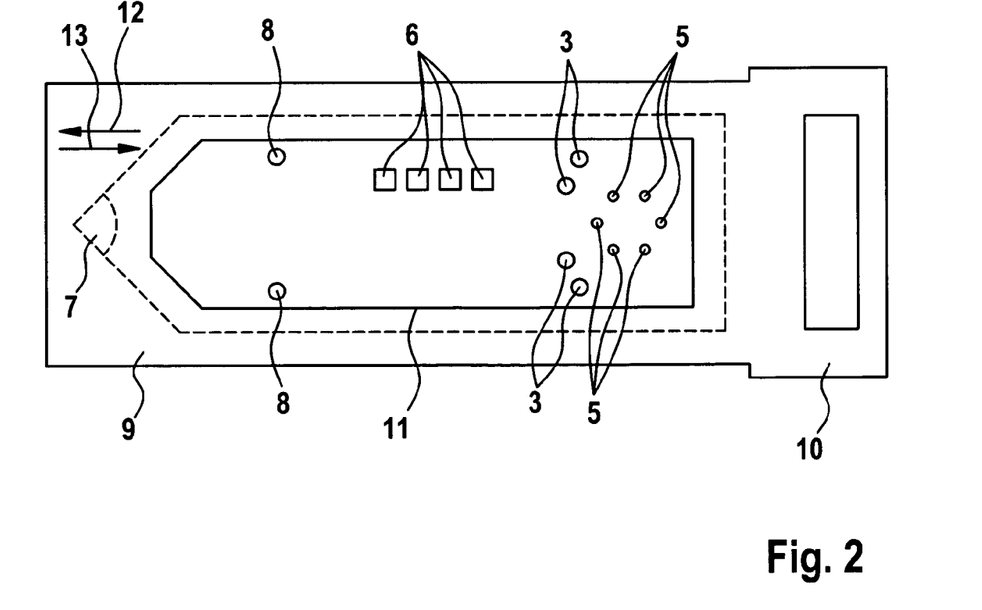
FIG. 2 depicts a microfluidic chip together with a support frame.

In the embodiment shown in FIG. 2, the polymeric microfluidic chip 1 has been inserted into a support frame 9 comprising a handle 10. The position of the microfluidic chip 1 is indicated with dashed lines. The support frame 9, which might e.g. be made of metal, comprises an opening 11, with the fluid ports 3, 5, the contact pads 6, and the through holes 8 being accessible via the opening 11.

In the embodiment of FIG. 2, the microfluidic chip 1 comprises a microspray nozzle 7. During operation, the microfluidic chip 1 is moved out (12) of the support frame 9. After operation has been finished, the microfluidic chip 1 is moved back (13) into the support frame 9, in order to avoid damages of the microspray nozzle 7.

Figure 3A:
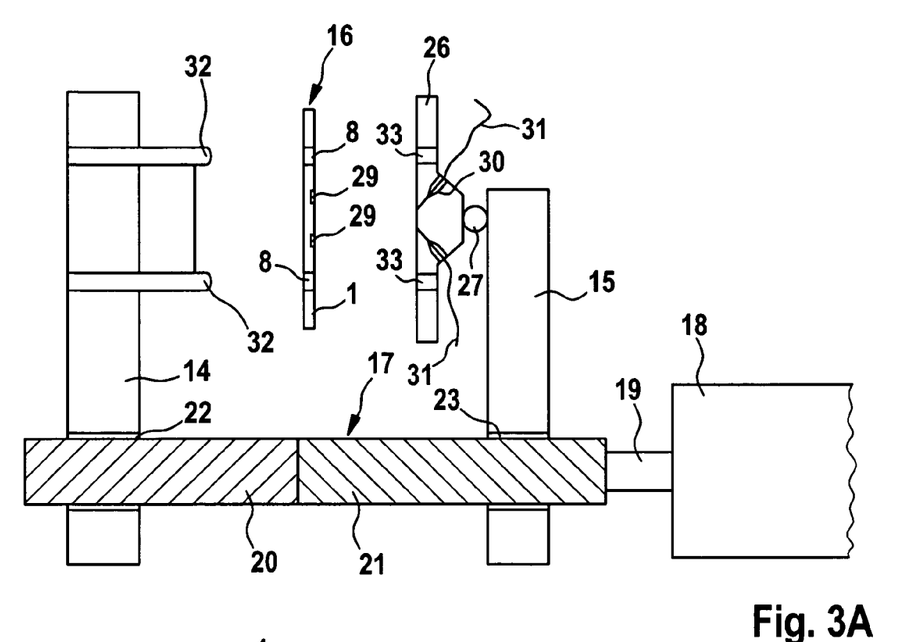
FIG. 3A shows a gripping device with clamping jaws being driven to their respective first positions.
Figure 3B:
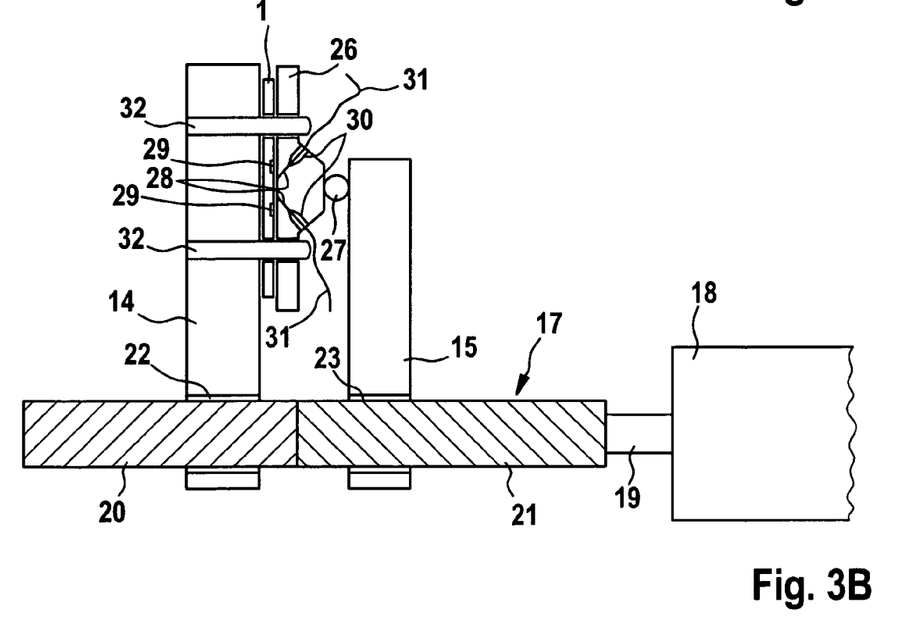
FIG. 3B shows the gripping device of FIG. 3A, with the clamping jaws being driven to their respective second positions.

FIGS. 3A and 3B show a gripping device adapting for fastening and releasing a microfluidic chip. The gripping device comprises a first clamping jaw 14 and a second clamping jaw 15, whereby the first and the second clamping jaw 14, 15 may be moved relative to one another using an actuation mechanism. In FIG. 3A, the first and the second clamping jaw 14, 15 are located at respective first positions. In their first positions, the two clamping jaws 14, 15 are spaced quite far apart from each other. Therefore, it is possible to place a microfluidic device 16 between the two clamping jaws 14, 15, or to remove a microfluidic device 16 from the gripping device.

In a first embodiment, the gripping device is adapted for fastening the microfluidic chip together with its support frame shown in FIG. 2. In an alternative embodiment, only the microfluidic chip 1 (without any support frame) might be fastened by the two clamping jaws 14, 15.

The actuating mechanism, which is adapted for moving the first and the second clamping jaw 14, 15 towards the microfluidic device 16, comprises a threaded rod 17 driven by a drive motor 18 via a drive shaft 19. Preferably, the drive motor 18 is implemented as a stepper motor, in order to allow for a precise control of the drive shaft's rotation. The threaded rod 17 comprises a first portion 20 with a right-handed thread, and a second portion 21 with a left-handed thread. The first clamping jaw 14 comprises a screw nut 22 that is engaged with the right-handed thread of the first portion 20. In the same way, the second clamping jaw 15 is provided with a screw nut 23 that is engaged with the second portion's left-handed thread. If the drive shaft 19 is rotated in a clockwise direction, the first clamping jaw 14 will be moved towards the microfluidic device 16, as indicated by arrow 24, and the second clamping jaw 15 will be moved in the direction of arrow 25. If the drive shaft 19 is rotated in a counterclockwise direction, both the first and the second clamping jaw 14, 15 will move away from the microfluidic device 16.

To the second clamping jaw 15, a stator plate 26 is mounted using a ball joint coupling 27. The ball joint coupling 27 provides for an angular adjustment of the stator plate 26 when the stator plate 26 is pressed onto the microfluidic device 16. The stator plate 26 comprises one or more fluid connectors 28 adapted for establishing fluid connections with corresponding fluid ports 29 of the microfluidic chip 1 when the stator plate 26 is pressed onto the microfluidic chip's surface. Each of the fluid connectors 28 is in fluid communication with a corresponding fitting 30 that permits attaching a respective capillary 31. Thus, different fluids may be supplied to and withdrawn from the fluid ports of the microfluidic chip 1 when the stator plate 26 is pressed towards the microfluidic chip's surface.

The first clamping jaw 14 comprises one or several alignment pins 32, with the ends of the alignment pins 32 being realized as tapered ends. The catch holes 8 of the microfluidic chip 1, which have already been shown in FIG. 1, 2, are located at positions that correspond to the respective positions of the alignment pins 32. The stator plate 26 comprises corresponding bore holes 33 as well. When both the first clamping jaw 14 and the second clamping jaw 15 are driven towards the microfluidic device 16, the alignment pins 32 will extend both through the catch holes 8 of the microfluidic device 16 and through the bore holes 33 of the stator plate 26, thereby providing for a precise alignment of the microfluidic device 16 relative to the gripping device.

FIG. 3B shows the gripping device after the two clamping jaws 14, 15 have been driven to their respective second positions, whereby both the first clamping jaw 14 and the second clamping jaw's stator plate 26 are pressed onto the surfaces of the microfluidic device 16. The alignment pins 32 extend through the catch holes of the microfluidic device 16 and the bore holes of the stator plate 26. Thus, the microfluidic device is gripped and tightly fastened at a predefined position relative to the gripping device.

The fluid connectors 28 are tightly pressed onto corresponding fluid ports 29 of the microfluidic chip 1, thereby establishing fluid-tight connections between the microfluidic chip's fluid passageways and the capillaries 31. Different fluids may either be provided to or withdrawn from the microfluidic chip.

In state of the art microfluidic chip devices, fluid pressures of 100 bar and above might be utilized, especially for conveying eluent and sample fluids through a separation column. Hence, fluids have to be supplied at pressures of 100 bar and above via the fluid connectors 28. In order to accomplish fluid-tight connections between the fluid connectors 28 and the corresponding fluid ports 29, the stator plate 26 has to be pressed against the microfluidic chip 1 with a predefined contact pressure, with the actuation mechanism being adapted for generating this predefined contact pressure.

For example, after both the first clamping jaw 14 and the stator plate 26 are already in contact with the microfluidic chip 1, the drive motor 18 might continue rotating the drive shaft 19 by force. As a consequence, the two clamping jaws 14, 15 will be deformed. Both the first clamping jaw 14 and the second clamping jaw 15 are bent in an outward direction and start to exert inbound forces 34, 35 upon the microfluidic chip 1. The inbound forces 34, 35 are due to the driving power of the drive motor 18. The inbound forces 34, 35 will tightly press the stator plate 26, which is preferably made of metal, against the microfluidic chip 1, which is preferably made of a polymeric material such as e.g. polyimide or PEEK. If the inbound forces 34, 35 are sufficiently large, the fluid connectors 28 will be tightly pressed against the fluid ports 29, and even if liquids are supplied at pressures of 100 bar and above, fluid-tight connections are established. The interface between a metal part and a polymeric material acts like a seal, and therefore, no extra sealing elements are necessary.

Additionally or alternatively to the fluid connectors 28 located at the stator plate 26, also the first clamping jaw 14 might comprise fluid connectors adapted for establishing fluid connections to the microfluidic chip 1.

Figure 4:
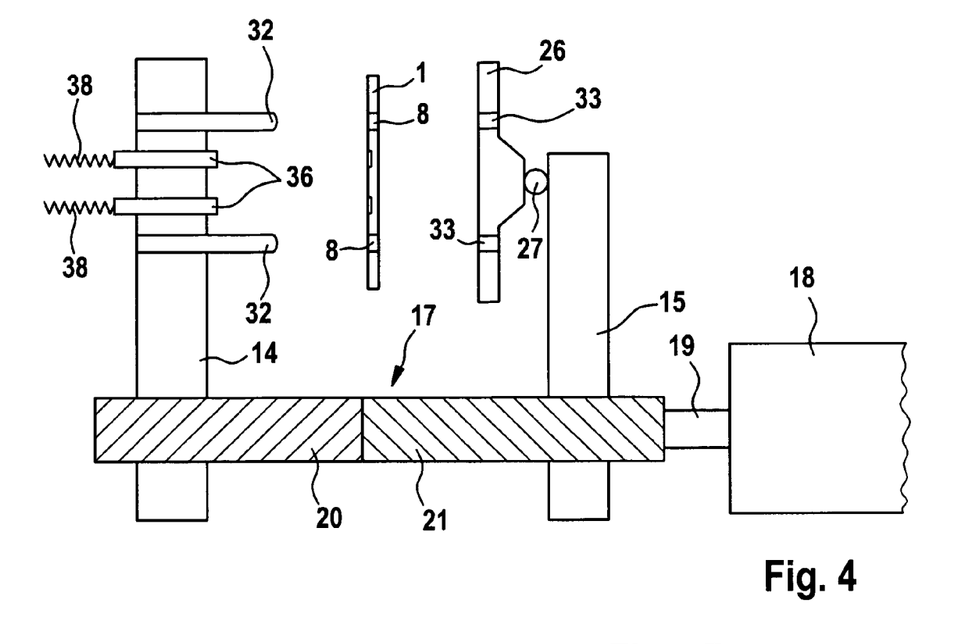
FIG. 4 shows the set-up of electrical connections using the clamping jaws.

In the embodiment of FIG. 4, it is shown how the gripping device can further be used for establishing electrical connections with the microfluidic chip 1. For this purpose, the first clamping jaw 14 comprises one or several contact pins 36. When the clamping jaws 14, 15 are driven towards the microfluidic chip 1, respective electrical connections are established between the contact pins 36 and corresponding contact pads 37 located on the microfluidic chip's surface. Preferably, the contact pins 36 are realized as spring-loaded contact pins, with the first clamping jaw 14 comprising one or several spring elements 38 for pressing the contact pins 36 against the corresponding contact pads 37. The spring force exerted by the spring elements 38 helps to establish reliable electrical connections.

Figures 5A, 5B:
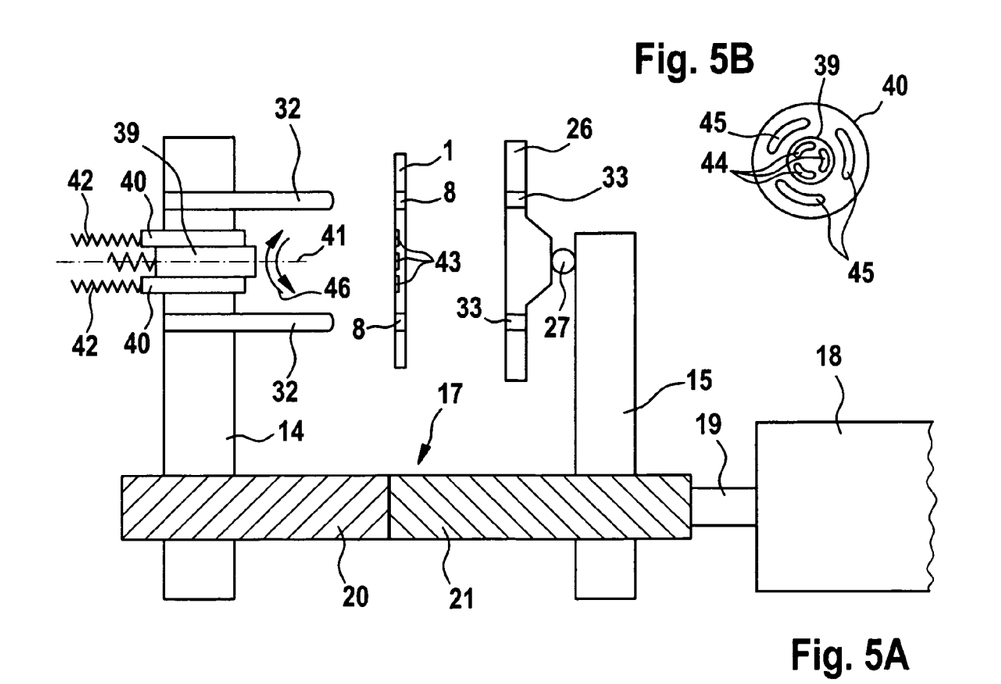
FIG. 5A shows a gripping device comprising one or more rotor elements.
FIG. 5B shows the face of a rotor element.

In the embodiment shown in FIG. 5A, the first clamping jaw 14 comprises an inner rotor element 39 and an outer rotor element 40, with the rotor elements 39, 40 being part of a multiport switching valve. The rotor elements 39, 40 can pivot on an pivot axis 41 between a plurality of rotor positions. Preferably, the rotor elements 39, 40 are realized as spring-loaded rotor elements arranged in a recess of the first clamping jaw 14, with the spring elements 42 being adapted for pressing the rotor elements towards the stator ports 43 of the microfluidic chip 1. FIG. 5B shows the front faces of the inner rotor element 39 and the outer rotor element 40. The inner rotor element 39 comprises three circumferential switching channels 44, with each of the switching channels 44 being adapted for providing fluid connections between adjacent stator ports 43. The outer rotor element 40 may be rotated independently of the inner rotor element 39. The outer rotor element 40 comprises three circumferential switching channels 45, with each of the switching channels 45 being adapted for providing switchable connections between adjacent stator ports 43.

When the first and the second clamping jaw 14, 15 are moved to their respective second positions shown in FIG. 3B, both the inner rotor element 39 and the outer rotor element 40 will be tightly pressed against the microfluidic chip 1. Even if fluid pressures of 100 bar and above are utilized on the microfluidic chip 1, the contact pressure exerted by the gripping device is sufficiently high for establishing fluid-tight connections between the rotor elements' switching channels 44, 45 and the fluid ports 43. Hence, after the microfluidic chip 1 has been fastened by the clamping jaws 14, 15, the user may switch between different flow paths of the microfluidic chip 1 by rotating (46) a respective one of the rotor elements 39, 40.

In yet another embodiment, which is not shown, at least one of the clamping jaws 14, 15 might further be equipped with one of the following: a thermal element, a heating element, a cooling element, a Peltier element. Preferably, a Peltier element is employed. In dependence on the voltage applied to the Peltier element, the Peltier element's front face is either heated up or cooled down. By driving the clamping jaws towards the microfluidic chip, the microfluidic chip is mechanically fastened, and the respective thermal element is brought in close contact with a predefined portion of the microfluidic chip. This embodiment might e.g. be used for cooling the microfluidic chip, or for depositing a certain amount of heat.

Figure 6:
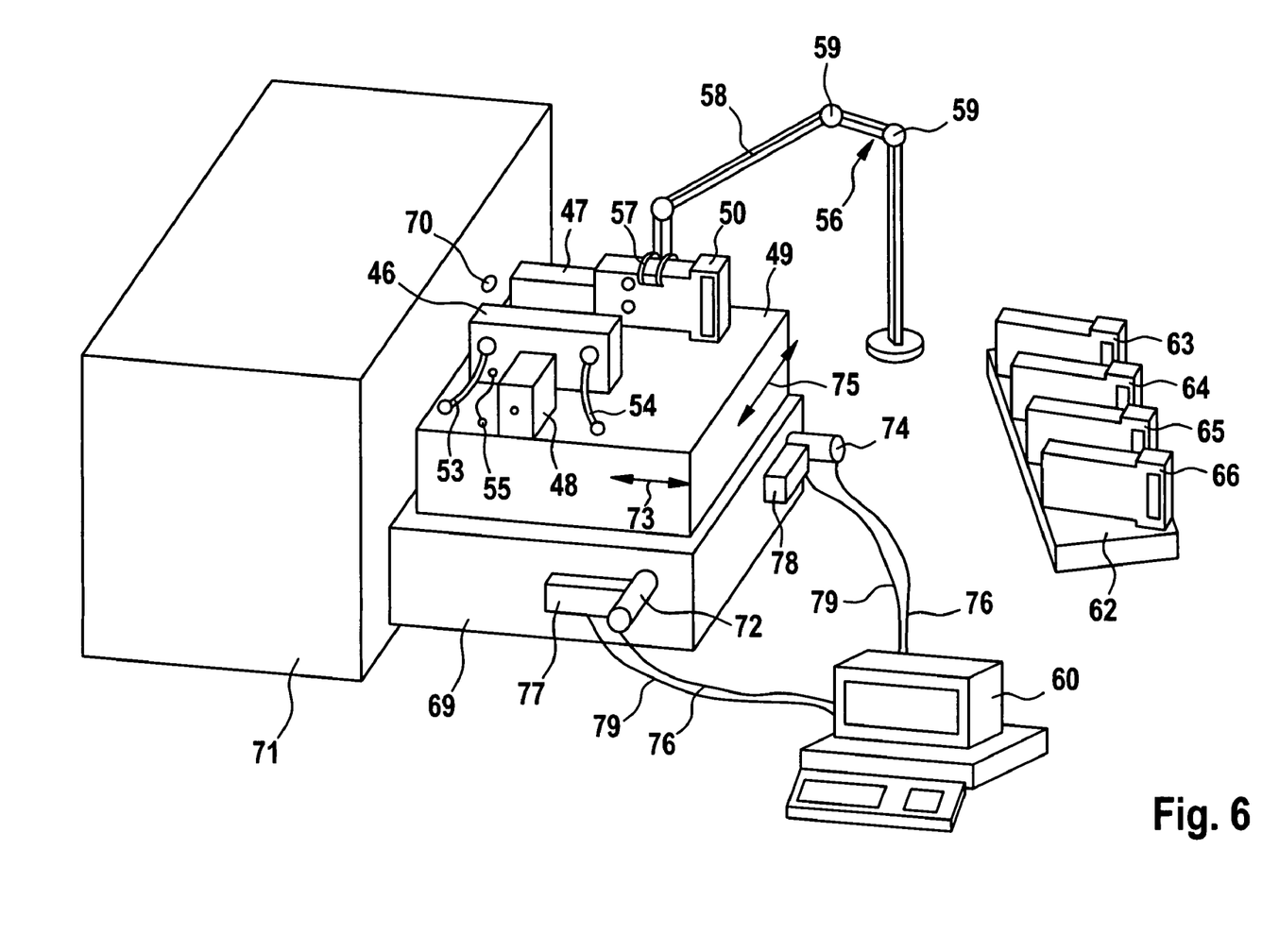
FIG. 6 shows a handling system comprising a robotic manipulator.

In the embodiment shown in FIG. 6, the above-described gripping device is employed as part of a handling system for microfluidic devices. The first clamping jaw 46, the second clamping jaw 47 and the actuation mechanism 48 are mounted on a base plate 49. When the two clamping jaws 46, 47 are driven to their respective first positions (cf. FIG. 3A) the microfluidic device 50 may be inserted between the two clamping jaws 46, 47. Then, the actuation mechanism 48 may drive the two clamping jaws 46, 47 to their respective second positions, as indicated by the arrows 51, 52. As a result, the microfluidic device 50 is gripped by the clamping jaws 46, 47. The clamping jaw 46 might be adapted for establishing at least one of hydraulic connections, electrical connections and thermal connections with the microfluidic device 50 when gripping the microfluidic device 50.

One or several fluid supply lines 53, 54 may be connected to the first clamping jaw 46, said fluid supply lines being adapted for at least one of: supplying different kinds of fluids to the microfluidic device 50, and withdrawing fluids from the microfluidic device 50. Furthermore, one or more electrical wires 55 might be connected to the first clamping jaw 46, in order to supply the required voltages and/or currents.

Furthermore, a robotic manipulator 56 may be part of the handling system. The robotic manipulator 56 might comprise a pair of gripping pliers 57 adapted for gripping and releasing microfluidic devices. The robotic manipulator 56 might further comprise an articulated arm 58 with a multitude of joint connections 59. The articulated arm 58 allows positioning the pair of gripping pliers 57 in the x-, y- and z-direction. Movements of the robotic manipulator 56 may be programmably controlled by a control unit 60, said control unit 60 being connected to the robotic manipulator 56 via a control bus 61.

The handling system might comprise a storage rack 62 that holds a multitude of microfluidic devices 63 to 66. The robotic arm 56 might select one of the microfluidic devices 63 to 66 stored in the storage rack 62, grip a selected device and transfer the respective microfluidic device to a location between the two clamping jaws 46, 47. There, the gripping pliers 57 release the microfluidic device, which is then fastened by the two clamping jaws 46, 47. Then, operation of the microfluidic device is started. After operation has been finished, the clamping jaws 46, 47 are driven back to their respective first positions, as indicated by the arrows 67, 68. Then, the robotic manipulator 56 may grip the microfluidic device, remove it from the location between the two clamping jaws 46, 47, and transfer it back to the storage rack 62. There, the robotic manipulator 56 releases the respective microfluidic device.

According to a preferred embodiment, the storage rack 62 might comprise microfluidic devices 63 to 66 of different types. For example, the microfluidic devices 63 to 66 might comprise different separation columns filled with different kinds of packing material. In dependence on the respective analytical task, the handling system may select a suitable one of the microfluidic devices 63 to 66, grip the selected device and move it to the clamping jaws 46, 47.

According to an alternative embodiment, the storage rack 62 might comprise several microfluidic devices of the same kind. Microfluidic devices are subjected to wear. For example, if the microfluidic chip comprises a separation column, the properties of the separation column might change in the course of time. Due to contamination, the flow conveyed through the separation column might become smaller and smaller, whereas with regard to pressure, an increase might be observed. Especially when performing a large number of measurements in series, it might become necessary to periodically replace the microfluidic device, in order to obtain reliable measurement results.

In order to replace a microfluidic device in due time, the handling system might comprise facilities for monitoring a feedback signal indicating wear of the microfluidic chip. For example, the microfluidic chip might comprise at least one of a pressure sensor or a flow sensor adapted for providing actual measurement of the fluid pressure and fluid flow on the microfluidic chip. Alternatively, the feedback signal might be obtained by evaluating measurement spectra recorded with a certain microfluidic device. The measurement spectra's signal-to-noise ratio is especially well-suited for indicating wear of the microfluidic device. In case the flow rates get too small, or in case the pressures get too high, or in case the signal to noise ratio is no longer acceptable, the control unit 60 might decide that the microfluidic chip should be replaced and instruct the robotic manipulator 56 accordingly. The robotic manipulator 56 will transfer the old microfluidic device back to the storage rack 62 and move a new microfluidic device to the gripping unit. As a result, a continuous operation is accomplished.

The handling system shown in FIG. 6 further comprises a positioning unit 69 that allows positioning the base plate 49, together with the clamping jaws 46, 47 and the actuation mechanism 48 mounted thereon, and together with a microfluidic chip that has been fixed in the gripping device. In particular, the positioning device 69 is adapted for positioning the microfluidic chip relative to an inlet 70 of a laboratory apparatus 71. For example, the microfluidic chip might comprise an electrospray nozzle 7, and the laboratory apparatus 71 might be a mass spectroscopy unit.

The positioning device 69 comprises a drive motor 72 for moving the base plate 49 in the x-direction (73), and a drive motor 74 for moving the base plate 49 in the y-direction (75). In a preferred embodiment, motion of the drive motors 72, 74 is controlled (76) by the control unit 60. In order to keep track of the base plate's actual position, the positioning device 69 might further comprise encoders 77, 78. The encoders 77, 78 are adapted for recording the base plate's movements, and for transmitting (79) positioning signals indicative of the base plate's position to the control unit 60. In accordance with the base plate's actual position, the control unit 60 might then generate suitable control commands for the drive motors 72, 74.

In a preferred embodiment, the handling system is used for positioning a microfluidic device relative to a mass spectroscopy unit. The microfluidic device comprises an electrospray nozzle that generates a stream of charged ions. After entering the mass spectroscopy unit, the stream of charged ions is attracted by a target electrode. Now, the microfluidic device is repositioned both in the x-direction 73 of FIG. 6 and in the y-direction 75 of FIG. 6. In dependence on the microspray nozzle's position, the ion current between the electrospray nozzle and the target electrode is detected. The voltage-current-characteristic of the electrospray current is used as a feedback signal, in order to reposition the microfluidic device in the best possible way.

What is claimed is:

1. A handling unit configured for handling a microfluidic device, the handling unit comprising:
   a first clamping element and a second clamping element,
   an actuation mechanism configured for driving at least one of the clamping elements,
   wherein, when the at least one of the clamping elements is driven to a first position, a microfluidic device is placed between the clamping elements or taken out of the clamping elements,
   wherein, when the at least one of the clamping elements is driven to a second position, the microfluidic device is gripped and fastened by relative movement of the clamping elements,
   the handling unit further comprising a positioning device configured for actively adjusting the position of the microfluidic device relative to at least one of the clamping elements while driving to the second position, and
   at least one of the clamping elements comprises connectors configured for supplying a liquid sample under pressure to the microfluidic device.

2. The handling unit of claim 1, wherein the clamping elements are pressed against the microfluidic device with a predefined contact pressure.

3. The handling unit of claim 1, wherein the actuation mechanism is configured for tightening the microfluidic device by driving the at least one of the clamping elements towards its second position, and
   wherein the actuation mechanism is configured for untightening the microfluidic device by driving the at least one of the clamping elements towards its first position.

4. The handling unit of claim 1, further comprising at least one feature selected from the group consisting of:
   the first clamping element is a stationary clamping element, and the second clamping element is a movable clamping element;
   the microfluidic device comprises a microfluidic chip supported by a frame;
   at least one of the clamping elements comprises alignment facilities configured for forcing the microfluidic device into a predefined position;
   at least one of the clamping elements comprises one or more alignment pins, said alignment pins being configured for extending into corresponding catch holes of the microfluidic device when the at least one of the clamping elements is driven towards its second position; and
   the actuation mechanism comprises one or more threaded rods configured for driving the at least one of the clamping elements into its predefined position, said threaded rods being driven by one or more stepper motors.

5. The handling unit of claim 1, wherein at least one of the clamping elements is adapted for establishing at least one connection selected from the group consisting of:
   one or several hydraulic connections with the microfluidic device,
   one or several electrical connections with the microfluidic device, and
   one or several thermal connections with the microfluidic device.

6. The handling unit of claim 1, wherein at least one of the clamping elements comprises one or more liquid connectors configured for establishing one or more liquid connections with corresponding liquid ports of the microfluidic device when the at least one of the clamping elements is driven towards the microfluidic device.

7. The handling unit of claim 1, further comprising at least one feature selected from the group consisting of:
   at least one of the liquid connectors is configured for supplying liquids at pressures of up to several hundred bar to the microfluidic device;
   the actuation mechanism is configured for pressing the clamping elements towards the microfluidic device with a predefined contact pressure, whereby the contact pressure exerted by the clamping elements provides for a liquid-tight coupling between liquid connectors of the clamping elements and liquid ports of the microfluidic device; and
   at least one of the clamping elements, when being driven towards the microfluidic device, acts as a spring bolt configured for exerting a predefined contact pressure onto the microfluidic device's surface.

8. The handling unit of claim 1, comprising at least one feature selected from the group consisting of:
   at least one of the clamping elements comprises one or more contact pins adapted for establishing one or more electrical connections with corresponding contacts of the microfluidic device when the at least one of the clamping elements is driven towards the microfluidic device; and
   at least one of the clamping elements comprises at least one element selected from the group consisting of: a heating element, a cooling element, a thermal element, and a Peltier element, with the respective element being pressed against the microfluidic device when the at least one of the clamping elements is driven towards the microfluidic device.

9. The handling unit of claim 1, further comprising at least one feature selected from the group consisting of:
   at least one of the clamping elements comprises a rotor plate with at least one rotor element;
   the rotor plate is supported by a ball joint coupling, with the ball joint coupling providing for an angular adjustment of the rotor plate when the clamping elements are pressed against the microfluidic device;

the rotor element is part of a multi-route selection valve;

the rotor element is a spring loaded rotor element arranged in a recess of the rotor plate; and at least one of the clamping elements comprises a stator plate, the stator plate being supported by a ball joint coupling, with the ball joint coupling providing for an angular adjustment of the stator plate when the clamping elements are pressed against the microfluidic device.

10. The handling unit of claim 1, further comprising at least one feature selected from the group consisting of:

the positioning device comprises one or more linear drives configured for positioning the clamping elements and a microfluidic device possibly contained therein;

the positioning device is configured for positioning the microfluidic device in accordance with a positioning signal;

the positioning signal is indicative of an actual position of the clamping elements;

the positioning signal comprises encoder signals related to the one or more linear drives;

the positioning device is configured for positioning the microfluidic device relative to a laboratory apparatus;

the positioning device is configured for positioning the microfluidic device relative to a mass spectrometry unit, with the positioning signal being derived from a sensitivity characteristic of the mass spectrometry unit;

the handling unit further comprises a storage rack configured for storing one or more microfluidic devices; and the storage rack contains a variety of different microfluidic devices suited for different analytical tasks, wherein in accordance with a respective analytical task, a suitable microfluidic device is selected.

11. The handling unit of claim 1, further comprising a robotic manipulator configured for performing at least one step selected from the group consisting of:

selecting one of a set of microfluidic devices contained in a storage rack;

gripping a microfluidic device from the storage rack; transferring the microfluidic device from the storage rack to a location between the first and the second clamping element;

placing the microfluidic device between the first and the second clamping element;

aligning the microfluidic device with the clamping elements;

removing a microfluidic device from the location between the clamping elements; and transferring the microfluidic device from the location between the clamping elements back to the storage rack.

12. The handling unit of claim 1, wherein the handling unit is configured for initiating replacement of a microfluidic device in accordance with a feedback signal.

13. The handling unit of claim 12, further comprising at least one feature selected from the group consisting of:

the feedback signal indicates wear of the microfluidic device;

the feedback signal indicates actual flow within the microfluidic device;

the feedback signal indicates actual fluid pressure within the microfluidic device; and the feedback signal indicates the quality of obtained measurement results, in particular a signal-to-noise level of acquired spectra.

14. The handling unit of claim 1, further comprising a control unit configured for generating control commands for at least one of the following devices:

the actuation mechanism, the positioning device, and the robotic manipulator device.

* * * * *